United States Patent
Ahlnäs

(10) Patent No.: US 10,765,712 B2
(45) Date of Patent: Sep. 8, 2020

(54) USE OF A COMPOSITION FOR LOWERING CHOLESTEROL LEVEL IN A MAMMAL, A METHOD FOR ITS PREPARATION AND A PRODUCT AND A FOOD ADDITIVE COMPRISING SAID COMPOSITION

(71) Applicant: Oy Granula Ab Ltd., Kotka (FI)

(72) Inventor: Thomas Ahlnäs, Kotka (FI)

(73) Assignee: Oy Granula Ab Ltd., Kotka (FI)

(*) Notice: Subject to any disclaimer, the term of this patent is extended or adjusted under 35 U.S.C. 154(b) by 0 days.

(21) Appl. No.: 16/208,597

(22) Filed: Dec. 4, 2018

(65) Prior Publication Data

US 2019/0117714 A1    Apr. 25, 2019

Related U.S. Application Data

(62) Division of application No. 15/373,764, filed on Dec. 9, 2016, now Pat. No. 10,172,896.

(60) Provisional application No. 62/264,887, filed on Dec. 9, 2015.

(51) Int. Cl.

| | | |
|---|---|---|
| A61K 36/00 | (2006.01) |
| A61K 36/15 | (2006.01) |
| A61K 31/365 | (2006.01) |
| A61K 31/09 | (2006.01) |
| A61K 31/341 | (2006.01) |
| A23L 33/105 | (2016.01) |
| A61K 9/08 | (2006.01) |
| A61K 31/56 | (2006.01) |
| A61K 45/06 | (2006.01) |
| A61K 31/05 | (2006.01) |
| A61K 31/34 | (2006.01) |
| A61K 47/10 | (2017.01) |

(52) U.S. Cl.
CPC ............ *A61K 36/15* (2013.01); *A23L 33/105* (2016.08); *A61K 9/08* (2013.01); *A61K 31/05* (2013.01); *A61K 31/09* (2013.01); *A61K 31/34* (2013.01); *A61K 31/341* (2013.01); *A61K 31/365* (2013.01); *A61K 31/56* (2013.01); *A61K 45/06* (2013.01); *A23V 2002/00* (2013.01); *A61K 47/10* (2013.01); *A61K 2236/33* (2013.01)

(58) Field of Classification Search
None
See application file for complete search history.

(56) References Cited

U.S. PATENT DOCUMENTS

2008/0057140 A1* 3/2008 Unkila ................ A61K 31/05
                                                       424/725
2010/0047294 A1* 2/2010 Ahlnas ................ A61K 8/97
                                                       424/401

* cited by examiner

*Primary Examiner* — Qiuwen Mi
(74) *Attorney, Agent, or Firm* — Berggren LLP

(57) ABSTRACT

A method to lower cholesterol level in a mammal blood serum is provided. A composition to lower the cholesterol levels and a method to make the composition is also disclosed. Food products with elongated shelf life as well as beneficial effects on human health are disclosed.

7 Claims, No Drawings

USE OF A COMPOSITION FOR LOWERING CHOLESTEROL LEVEL IN A MAMMAL, A METHOD FOR ITS PREPARATION AND A PRODUCT AND A FOOD ADDITIVE COMPRISING SAID COMPOSITION

PRIORITY

This application is a divisional of non-provisional application Ser. No. 15/373,764, filed on Dec. 9, 2016, which claims the priority of U.S. provisional application 62/264,887 filed on Dec. 9, 2015, the contents, of all of which, are incorporated herein by reference.

FIELD OF THE INVENTION

This invention relates to wood lignans and their use in food and feed industry. The invention also relates to method of making wood lignan comprising compositions.

The present invention relates to use of a lignan mixture according to appended claims for lowering cholesterol level of blood in a mammal.

The invention relates also to a method for preparing said lignan mixture.

Additionally, the invention relates to a product for lowering cholesterol level in a mammal comprising said lignan mixture.

The invention also relates to a food additive and a food product containing said lignan mixture.

In the field of food products there is a continuous demand for new dietary supplements having beneficial effect on human health. This demand arouses on the one hand from the fact that food products are often so called convenience food products which lack many essential nutrients and may contain additionally modified fatty acids, so called trans-fatty-acids, which have unfavourable effect on triglyceride levels and content of blood serum. On the other hand a big chunk of modern diet contains animal based food products (meat, milk, butter, cheese etc.) which contain saturated fats having unfavourable effect on blood triglyceride content and which increase blood cholesterol level.

Plant lignans are the primary source of dietary phytoestrogens in modern diet. Phytoestrogens have multitude beneficial health effects; high levels of lignans can support for example healthy glucose metabolism, reduce insulin sensitivity. They have suggested also to be used for treating general infections and inflammations (see U.S. Pat. No. 5,762,935) when used as dietary supplement.

However, plants (fruits, vegetables and seeds) contain so low levels of lignans that their health effects in normal diet is almost insignificant. The lignan content of foods is generally low and usually does not exceed 2 mg/100 g. They have been suggested to be as dietary supplement in the range of about 0.5-10 wt-%.

Wood lignans are very abundant in wood material and bark and thus one might consider using these lignans in the diet in the same way as plant lignans. It has been suggested to use wood lignans in food based on their antioxidative effect and some wood lignans science have also been found to be effective against cancer(s). However, wood lignans and extracts containing wood lignans have usually a dark colour and a bitter aftertaste, which have effectively prevented their usage as a food additive.

For these reasons wood lignans have been used only in the field of cosmetics, which use is based mainly on their antioxidative and antimicrobial effect. For example, the applicant has earlier presented some wood lignan mixture(s) to be used in various cosmetics products to enhance the effect and safety of UV-protective agent used therein.

Based on the above mentioned prior art the inventors set a task to study the use of wood lignans especially in the diet for gaining new healthy food products.

Therefore, the main objective of the present invention is to find new uses for wood lignans.

The second objective of the invention was to find new uses for wood lignans in spite of their somewhat negative properties as to their colour and taste.

The third objective of the invention is to find a simple method for preparing lignan based ingredients to be used as food additives and food grade components, which can be added into food products.

Yet another objective of the invention is to provide novel products improving production of beneficial compounds in the human digestive system by bacterial flora in the gut.

These and other objects and features of the invention will be apparent from the following description and the claims.

Firstly, the present invention is based on the very surprising observation that certain lignan mixture comprising at least following lignans: 7-hydroxymatairesinol, conidendrin, lariciresinol, liovil and secoisolariciresinol or their geometric isomers or stereoisomers thereof, have a very significant blood cholesterol lowering effect when these lignan mixtures are used as a dietary supplement for a mammal. The concentration of lignan mixture should be 1-50 wt-% of said compound used as a food additive. Preferably the concentration of lignan mixture is 5-50 wt % of the total weight of a food additive.

Due to its considerable blood cholesterol lowering effect, the wood lignan mixture can be used in relatively small quantities; normal daily dietary portion of lignan mixture is 30-50 mg. When the lignan mixture is used as an alcohol-wood extract or alcohol-water-wood extract containing 1-5% lignan mixture, its daily usage can be kept as low as 5-10 droplets.

Present invention is very surprising because this combination of wood lignans have not been known to have any blood cholesterol effect and since this effect is unmatched compared to known plant lignans; daily diet of most humans include plant lignans which have similar properties, for example antioxidative properties as wood lignans. However, the level of lignans is usually very low in edible plants and therefore their possible beneficial cholesterol lowering effect has not been detectable. Moreover, the suggested usage level of plant lignans in food additives is also comparatively high.

Secondly, the present invention is based on the fact that the phenolic compounds, such as lignans, tannins and flavonoids contained in the wood material, are extracted from the wood with an extraction medium, which as such is suitable for various food products. Extraction medium may be an extraction solution or subcritical or supercritical extraction fluid, such as $CO_2$. In the previous practice of the art, lignans, tannins and flavonoids have been purified before using them in food industry.

Differing from said previous practice in the art, the invention is based on the fact that the raw extraction solution or extraction fluid is not purified before use. The raw extraction solution-wood extract or raw extraction fluid-wood extract is recovered from the wood material, such as wood chips or chipped wood pulp of the chemical pulp industry, which contain lignans and/or flavonoids and/or tannins as active ingredients and is then used as such for preparing various food products, food additives or semi-finished products usable in food products.

In a case this composition according to invention being a solution composing of extraction liquid-wood extract the relative amounts of active ingredients in lignan mixture maybe modified for better suiting in a designed use. This can be obtained, for example by a fractionating extracting procedure. The solvent to be used as an extraction solution may be simply selected on the basis of its suitability to further use.

This provides the advantage that the isolation of the raw extraction solution-wood extract or raw extraction fluid-wood extract from the wood material is simple and requires a considerably smaller number of process stages than before.

The raw extraction solution-wood extract maybe a mixture that originates in two or more tree species, such as spruce and pine or conifer and birch. The wood may originate from trees belonging to genus *Picea* or genus *Abies*. The wood may originate specifically from *Picea* sp, *Tsuga* sp. (hemlock) or *Acacia* sp. Additionally *Betula* sp. may be used. The types and amounts of lignans obtained from different wood species vary considerably. By adding lignans from other wood species or plants one might modify the effect of lignan mixture (=active ingredient).

Thirdly, the invention is based on the fact that the selection of active ingredients incorporated into food additives or food grade components should be designed so, that they can affect to various human body parts. Human body contains various polar, semi-polar, and non-polar elements, tissues, organs and membranes.

Therefore, the active ingredients should contain a mixture of various lignans, each having different polarity. Examples of the various elements of the body, which require active ingredients that have different migration: cell wall (semi-polar), the exterior of the cell, water phase (polar), and hydrophobic elements (the body tissues that contain fat).

The present lignans seem to lower cholesterol level by preventing inflammation of blood vessel. If only one purified lignan compound would be used as the active ingredient, its migration into walls of blood vessels in the different places of the body would be considerably weaker than those of the active ingredient mixture (=lignan mixture) according to the invention.

Therefore, the invention according to claim 1 relates to the use of a lignan mixture for lowering cholesterol level of a blood serum in a mammal such as human.

To be more exact the present invention relates to the use of a composition comprising at a range of 1-50 wt-% preferably at a range of 5-50 wt-% of a lignan mixture comprising at least following lignans: 7-hydroxymatairesinol, conidendrin, lariciresinol, liovil and secoisolariciresinol or their geometric isomers or stereoisomers thereof for lowering cholesterol level of blood serum in a mammal.

The percent ranges given for lignan mixture means percent by weight, based on the total composition.

The invention relates also to a product according to claim 12 for lowering cholesterol level of a blood serum in a mammal.

To be more exact the present invention relates to the product for lowering cholesterol level of a blood serum in a mammal, which comprises at a range of 1-90 wt-% preferably at a range of 5-90 wt-% a lignan mixture comprising at least following lignans: 7-hydroxymatairesinol, conidendrin, lariciresinol, liovil and secoisolaricresinol or their geometric isomers or stereoisomers thereof in a combination with an extraction solution selected from the group composing of alcohol and water-alcohol mixture the balance being a physiologically acceptable carrier agent.

The percent ranges (wt %) given for lignan mixture means percent by weight, based on the total product composition.

One important aspect of the invention is also to make wood lignans available in such a level in an edible food product that their concentration is high enough to ensure that their beneficial blood serum cholesterol level lowering effect will appear. Normal wood material contains only small amounts of wood lignans and making food supplements from this kind of wood material would be cumbersome and ineffective. However wood bark and knot wood have been founded to include much higher amounts of these lignans which make mentioned lignan mixture.

Therefore one important aspect of the invention relates to a method for preparing composition for lowering cholesterol level in a mammal blood serum using wood bark or knot wood as source of lignans.

Thus, the method according to claim 6 relates to a method for preparing composition for lowering cholesterol level of blood serum in a mammal.

To be more exact the present invention relate to a method for preparing composition for lowering cholesterol level of blood serum in a mammal, said composition comprising at a range of 1-50 wt-%-% preferably 5-50 wt-% of lignan mixture comprising at least following lignans: 7-hydroxymatairesinol, conidendrin, lariciresinol, liovil, secolsolariciresinol or their geometric isomers or stereoisomers thereof to be used which method comprises at least the following steps:

extracting knot wood or bark with an extraction solution selected from the group composed of alcohol and water-alcohol mixture, for getting an alcohol-wood extract or alcohol-water-wood extract, adding a physiologically acceptable carrier agent to said alcohol-wood extract or alcohol-water-wood extract.

Present invention relates also to a food additive, nutraceutical or dietary supplement for lowering cholesterol level of blood serum in a mammal.

To be more exact the present invention relates to an additive for a food product for lowering cholesterol level of blood serum in a mammal, said additive comprising at a range of 1-50 wt-%, preferably 5-50 wt-% a lignan mixture comprising at least following lignans: 7-hydroxymatairesinol, conidendrin, lariciresinol, liovil and secoisolariciresinol or their geometric isomers or stereoisomers thereof in combination with an edible solid or liquid carrier material.

Preferably said food additive comprises at a range of 1-90 wt-% preferably at a range of 5-90 wt-% said lignan mixture in a combination with an extraction solution selected from the group composing of alcohol and water-alcohol mixture the balance being an edible solid or liquid carrier material.

The spectrum of effect of lignan mixture can be widened by adding other wood lignans or triterpenes having for example different antimicrobial potency than said lignan mixture.

Therefore the invention also relates to the use of composition further comprising stilbenes or triterpenes selected from the group composed of betulin, betulonic acid, betulinic acid, betuloinic acid, resveratrol and their geometric isomers or stereoisomers thereof. The invention relates also to corresponding food additives and products containing this kind of stilbenes or triterpenes.

In this connection it should also be noted, that the lignan mixture in itself has antimicrobial potency. Therefore the invention relates also to extend the shelf life of a food material by mixing said food material with a food additive containing above mentioned lignan mixture obtained from wood material.

Furthermore, the composition according to present invention may contain also other lignans obtained from other sources, such as various plant lignans. Additionally composition can contain antioxidants such as vitamins, or substances for treating illnesses or to be used as microbicides (betulinic acid or betuline obtained from birch). When this kind of compounds are used in food products they can obtain new properties; they are either better for human health or they might even be helpful in preventing development of illnesses (so called health food). By extracting of different types of wood or plants, active ingredient mixtures are obtained having different properties, such as antioxidative, microbicidal and, possibly, disease-preventive, and abilities to catch free radicals.

It is known that lignan glycosides are absorbed in the gastrointestinal tract after metabolism by intestinal bacteria to lignan aglycones and the enterolignans (enterolactone and enterodiol), which are formed from them. Both enterolactone and enterodiol have been shown to possess weakly estrogenic and antiestrogenic activities, and it has been suggested that the high production of these antiestrogenic mammalian lignans in the gut may serve to protect against breast cancer in women and prostate cancer in men. Thus the composition of this invention may further be used as a prophylactic composition to prevent development of cancerous diseases.

The food additive is preferably formulated so that lignan mixture and a carrier material form together an encapsulated liquid, powder or pill.

Typically the food additive according to present invention is added into various oils such as sauces, salad dressings, marinades.

These food additives can also be mixed into various convenience foods and ready meals which may additionally be based on meat. Often these convenience foods or ready meals comprise so called "junk food" such as hamburgers, French fries etc. which have low level of nutrients and lot of modified fatty acids, so called trans-fatty-acids and/or saturated meat based fats. By adding food additives, or dietary supplements comprising mentioned (wood) lignan mixture these "junk foods" can be made somewhat healthier.

The food additive according to the invention may be added also into plant based food products which have none or very few plant lignans. These are for example rice, pasta, macaroni and bread.

If the food additive according to present invention is added into bread one can increase its health values but also its shelf life. The latter effect is of big significance because adding shelf life of bread will influence positively to whole distribution logic.

The food additive according to present invention can also be added into various drinks, juices and nectars.

The food additive according to present invention may also have beneficial effect if one wishes a bit bitter taste to food.

Preferably the lignan mixture used in the products, compounds and food additives according to the invention is obtained by extracting or grinding knot wood of coniferous trees, which belong to wood genus *Picea* or *Abies*. If this lignan mixture has been obtained from knot wood of genus *Picea*, or *Abies*, its lignan mixture has the following formula:
  7-hydroxymatairesinol 70-80%;
  conidendrin 3-8%;
  lariciresinol 1-4%;
  liovil 2-5%;
  secoisolarisinol 3-7%
  other lignans 0-3%.

Usually this lignan mixture contains also oligolignans.

Depending on the source of wood material it may contain also other wood lignans such as pinoresinol, nortrachelogenin, matairesinol and juvabiones.

For extracting of knot wood and/or bark with an extraction solution, for obtaining an alcohol-wood extract or an alcohol-water-wood extract, various alcohol-based solvents, such as butylene glycol, butylene glycol+monoalcanol, glycerol or glycerol+alcohol can be used. These alcohol based solvents are either physiologically acceptable or/and edible.

The extraction solution preferably contains a lower monovalent or bivalent alkyl alcohol or a mixture of the lower monovalent and bivalent alkyl alcohols and/or glycerol, or a mixture of the lower (monovalent) alkyl alcohol and the bivalent or a trivalent lower alkyl alcohol.

The monovalent alcohol is preferably ethanol, propanol, butanol, heptanol, octanol or decanol. The monoalcohol is especially preferably ethanol.

The bivalent alkyl alcohol is preferably a lower alkylene glycol, which is preferably selected from a group composing of ethylene glycol, propylene glycol, butylene glycol, pentylene glycol, and dipropylene glycol. Butylene glycol is an especially preferable solvent, as the lignan mixture according to the invention dissolves therein in amounts of over 10% and it is physiologically tolerable. Solutions of ethanol and bivalent alcohols are preferable for dissolving and also extracting the lignan mixtures according to the invention. Bivalent alcohol is especially preferably selected from the group composing of ethylene glycol, propylene glycol, butylene glycol, pentylene glycol, dipropylene glycol.

Suitable trivalent alcohol solvents are glycerols.

The mixture of the lower alkyl alcohol and glycerol or alkyl glycol is a preferable solvent medium, as the need to further process the raw extracts (=solvent+active ingredient mixture) or raw extract concentrates based on extraction solutions containing such alcohols is as small as possible, when preparing different food additives or food grade compositions.

The alcohol or water-alcohol based raw alcohol-wood extracts or alcohol-wood extracts are well-suited to the manufacture of food-grade components or to be used as such. These food grade components include, without limiting to them, emulsions, dispersions, oils, sweeteners.

Lignan mixtures of the present invention can be added as an alcohol-wood extracts or alcohol-water-wood extracts into various food additives or food grade compositions made of these extracts.

Food additives are selected from the group consisting of feed ingredients, food supplements, and food additives for direct human consumption.

A food supplement includes vitamins and mineral supplements in unit dose forms such as capsules, tablets, powders, solutions etc. This page provides information on the food additive provisions that are acceptable for use in foods conforming to the food category. A comprehensive list of possible food supplements in which the lignan mixture of the present invention can be used, has been presented in GSFA online Food Category.

A feed ingredient is a component part or constituent or any combination/mixture added to and comprising the feed. Feed ingredients might include grains, milling byproducts, added vitamins, minerals, fats/oils, and other nutritional and energy sources. A comprehensive list of feed ingredients has been presented in the Official Publication of the Association of American Feed Control Officials (AAFCO).

A comprehensive list of food additives in which the present lignan mixture can be included has been presented in CFR Code of Regulations Title 21. These includes food preservatives (subpart A), food coatings (subpart C), special dietary and nutritional additives (subpart D), anticaking agents (subpart E), flavoring agents and related substances (subpart F), gums, chewing gum bases and related substances (subpart G), other specific usage additives (subpart H), multipurpose additives (subpart I).

Some examples of food grade compositions or food additives into which the alcohol or water-alcohol based raw alcohol-wood extracts or alcohol-wood extracts can be mixed and which belong to above mentioned multipurpose additives (subpart I) of CFR Code of Federal Regulations Title 21:
172.809 Currdlan.
172.810 Dioctyl sodium sulfosuccinate.
172.811 Glyceryl tristearate.
172.812 Glycine.
172.814 Hydroxylated lecithin.
172.816 Methyl glucosidecoonut oil ester.
172.818 Oxystearin.
172.820 Polyethylene glycol (mean molecular weight 2009, 500).
172.822 Sodium lauryl sulfate.
172.824 Sodium mono and dimethyl naphthalene sulfonates.
172.826 Sodium stearyl fumarate.
172.828 Acetylated monoglycerides.
172.829 Neotame.
172.830 Succinylated monoglycerides.
172.831 Sucralose.
172.832 Monoglyceride citrate.
172.833 Sucrose acetate isobutyrate (SAIB).
172.834 Ethoxylated mono and diglycerides.
172.836 Polysorbate 60.
172.838 Polysorbate 65.
172.840 Polysorbate 80.
172.841 Polydextrose.
172.842 Sorbitan monostearate.
172.844 Calcium stearoyl-2-lactylate.
172.846 Sodium stearoyl lactylate.
172.848 Lactylic esters of fatty acids.
172.850 Lactylated fatty acid esters of glycerol and propylene glycol.
172.852 Glyceryl lacto esters of fatty acids.
172.854 Polyglycerol esters of fatty acids.
172.856 Propylene glycol mono and diesters of fats and fatty acids.
172.858 Propylene glycol alginate.
172.859 Sucrose fatty acid esters.
172.860 Fatty acids.
172.861 Cocoa butter substitute from coconut oil, palm kernel oil, or both oils.
172.862 Oleic acid derived from tall oil fatty acids.
172.863 Salts of fatty acids.
172.864 Synthetic fatty alcohols.
172.866 Synthetic glycerin produced by the hydrogenolysis of carbohydrates The present lignan mixture of the present invention can also be mixed with carrier or extraction solvents which are appropriate food additives. The lignan mixture can be either powder or alcohol-water-wood extract or alcohol-wood extract.

A comprehensive list of these carrier or extraction solvents can be found from health Canada, Food and Nutrition. These carrier or extraction solvents include following: acetone, benzyl alcohol, 1,3-butylene glycol, carbon dioxide, castor oil, citric acid esters of mono- and diglyserides, ethyl acetate, ethanol, glycerol (glyserin), glyceryl diacetate, glyceryl triacetate, glyceryl tributyrate, hexane, isopropanol alcohol, methyl alcohol, methyl ethyl ketone(2-butanone), methylene chloride, mono- and diglycerides, monoglyceride citrate, 2-nitropropane, 1,2-propylene glycol (1,2-propanediol), propylene glycol monoesters and diesters of fatforming fatty acids, triethyl citrate.

Certain embodiments are related to a method to lower cholesterol level in blood serum of a mammal by administering three to ten droplets daily for a period of two to twelve months of a composition comprising at a range of 1-50 wt-%, preferably at a range of 5-50 wt-% a lignan mixture comprising at least following lignans: 7-hydroxymatairesinol, conidendrin, lariciresinol, liovil and secoisolariciresinol or their geometric isomers or stereoisomers thereof.

Certain further embodiments are related to the methods to lower cholesterol level in blood serum of a mammal wherein the lignan mixture comprises additionally one or more lignan(s) at a range of 0-10 wt-% selected from the group composing of: pinoresinol, nortrachelogenin, matairesinol, juvabiones, or their geometric isomers or stereoisomers thereof and oligolignans.

Certain further embodiments are related to the methods to lower cholesterol level in blood serum of a mammal wherein the composition further comprises stilbenes or triterpens selected from the group consisting of betulin, betulonic add, betulinic acid, betuloinic acid, resveratrol, their geometric isomers and stereoisomers thereof.

Certain further embodiments are related to the methods to lower cholesterol level in blood serum of a mammal wherein the composition further comprises vitamins or plant lignan (s).

Certain further embodiments are related to the methods to lower cholesterol level in blood serum of a mammal wherein inflammation of blood vessels is prevented.

Certain embodiments are related a method for preparing composition for lowering cholesterol level of blood serum in a mammal, said composition comprising at a range of 1-10 wt-% preferably 5-50 wt-% lignan mixture comprising at least following lignans: 7-hydroxymatairesinol, conidendrin, lariciresinol, liovil, secoisolariciresinol, their geometric isomers or stereoisomers thereof, wherein the method comprises the following steps:
a) extracting knot wood and/or bark with an extraction solution selected from the group consisting of alcohol and alcohol-water mixture,
b) obtaining an alcohol-wood extract or an alcohol-water-wood extract, and
c) adding a physiologically acceptable carrier agent to said alcohol-wood extract or alcohol-water-wood extract.

Certain further embodiments are related to the method for preparing composition for lowering cholesterol level of blood serum in a mammal, wherein the composition comprises additionally one or more lignan(s) at a range of 0-10 wt-% selected from the group consisting of pinoresinol, nortrachelogenin, matairesinol, juvabiones, oligolignans, their geometric isomers and stereoisomers thereof.

Certain further embodiments are related to the methods for preparing composition for lowering cholesterol level of blood serum in a mammal, wherein the alcohol is a lower monovalent alcohol, a lower bivalent alkyl alcohol or a lower trivalent alcohol or mixture thereof.

Certain further embodiments are related to the methods for preparing composition for lowering cholesterol level of blood serum in a mammal, wherein the bivalent alkyl alcohol is selected from the group consisting of propylene glycol, butylene glycol and pentylene glycol, and the trivalent alcohol is glycerine.

Certain further embodiments are related to the methods for preparing composition for lowering cholesterol level of blood serum in a mammal, wherein the knot wood originates from coniferous trees selected from genus *Picea, Abies* or *Tsuga*.

Certain further embodiments are related to the methods for preparing composition for lowering cholesterol level of blood serum in a mammal, wherein the knot wood originates from *Picea abies*, hemlock (*Tsuga* sp.) or from *Acacia* sp.

Certain embodiments are related to a product for lowering cholesterol level of blood serum in a mammal, said product comprising at a range of 1-90 wt-%, preferably at a range of 5-90 wt-%, a lignan mixture comprising in an extraction solution at least the following lignans: 7-hydroxymatairesinol, conidendrin, lariciresinol, liovil and secoisolariciresinol, or their geometric isomers or stereoisomers thereof, wherein the extraction solution is selected from the group consisting of an alcohol and water-alcohol mixture, the balance being a physiologically acceptable carrier agent.

Certain embodiments are related to a product for lowering cholesterol level of blood serum in a mammal, said product comprising at a range of 1-50 wt-%, preferably at a range of 5-50 wt-%, a lignan mixture comprising at least following lignans: 7-hydroxymatairesinol, conidendrin, lariciresinol, liovil and secoisolariciresinol or their geometric isomers or stereoisomers.

Certain further embodiments are related to the products for lowering cholesterol level of blood serum in a mammal wherein the product additionally comprises one or more lignan(s) at a range of 0-10 wt-% selected from the group consisting of pinoresinol, nortrachelogenin, matairesinol, juvabiones, their geometric isomers or stereoisomers, and oligolignans.

Certain further embodiments are related to the products for lowering cholesterol level of blood serum in a mammal wherein extraction solution comprises monovalent lower alcohol such as ethanol and/or, divalent lower alcohol such as propanediol and/or trivalent lower alcohol such as propanetriol.

Certain further embodiments are related to the products for lowering cholesterol level of blood serum in a mammal, wherein concentration of said lignans is following:
  7-hydroxymatairesinol 70-80%;
  conidendrin 3-8%;
  lariciresinol 1-4%;
  liovil 2-5%;
  secoisolarisinol 3-7%; and
  other lignans 0-3%.

Certain further embodiments are related to the products for lowering cholesterol level of blood serum in a mammal, wherein the product further comprises triterpens or stilbenes selected from the group consisting of betulin, betulonic acid, betulinic acid, betuloinic acid, resveratrol, their geometric isomers and stereoisomers thereof.

Certain further embodiments are related to the products for lowering cholesterol level of blood serum in a mammal, wherein the product further comprises vitamin(s) or plant lignan(s).

Certain embodiments are related to a food additive for extending shelf life of a food product comprising at a range of 1-50 wt-%, preferably 5-50 wt-% a lignan mixture comprising at least following lignans: 7-hydroxymatairesinol, conidendrin, lariciresinol, liovil, secoisolariciresinol, their geometric isomers or stereoisomers thereof in combination with an edible solid or liquid carrier material.

Certain embodiments are related to the food additives for extending shelf life of a food product further comprising at a range of 1-90 wt-%, preferably at a range of 5-90 wt-% said lignan mixture in a combination with an extraction solution selected from the group consisting of alcohol and water-alcohol mixture the balance being an edible solid or liquid carrier material.

Certain further embodiments are related to the food additives, wherein the additive is in a form of a liquid, or a powder.

Certain further embodiments are related to food products comprising the food additives of the previous embodiments.

Certain further embodiments are related to the food products of the previous embodiments, wherein the food product is a baking product or a meat product.

Certain further embodiments are related to the food products of the previous embodiments, wherein the baking product is a bread, a cake or a pastry.

Certain embodiments are related to a food additive, dietary supplement or nutraceutical for lowering cholesterol level of blood serum in a mammal, said dietary supplement comprising at a range of 1-50 wt-%, preferably 5-50 wt-% a lignan mixture comprising at least following lignans: 7-hydroxymatairesinol, conidendrin, lariciresinol, liovil, secoisolariciresinol, their geometric isomers or stereoisomers thereof in combination with an edible solid or liquid carrier material.

Certain embodiments are related to the food additive, dietary supplement or nutraceutical for lowering cholesterol level of blood serum in a mammal further comprising at a range of 1-90 wt-%, preferably at a range of 5-90 wt-% said lignan mixture in a combination with an extraction solution selected from the group consisting of alcohol and water-alcohol mixture the balance being an edible solid or liquid carrier material.

Certain further embodiments are related to the food additive, dietary supplement or nutraceutical for lowering cholesterol level of blood serum in a mammal wherein the supplement is in a form of a liquid, pill, capsule or powder.

Certain further embodiments are related to the food additive, dietary supplement or nutraceutical for lowering cholesterol level of blood serum in a mammal wherein it is added to a food product.

Certain embodiments are related to a fortified food product comprising the food additive, dietary supplement or nutraceutical for lowering cholesterol level of blood serum in a mammal.

Certain further embodiments are related to the food additives or dietary supplements or nutraceuticals of any of the previous embodiments, wherein said lignan mixture comprises also one or more lignan(s) at a range of 0-10 wt-% selected from the group composing of: pinoresinol, nortrachelogenin, matairesinol, juvabiones and oligolignans, and their geometric isomers or stereoisomers thereof.

Certain further embodiments are related to the food additives or dietary supplements or nutraceuticals of any of the previous embodiments, wherein the additive, supplement or nutraceutical further comprises stilbenes or triterpenes selected from the group composed of betulin, betulonic acid, betulinic acid, betuloinic acid, resveratrol and their geometric isomers or stereoisomers thereof.

Certain further embodiments are related to the food additives or dietary supplements or nutraceuticals of any of the previous embodiments, wherein the additive or the supplement further comprises vitamins or plant lignan(s).

Certain further embodiments are related to the fortified food products of any of the previous embodiments, wherein, wherein the product is emulsion or liquid such as oil, sauce, dressing, yoghurt, juice, nectar or drink.

Certain further embodiments are related to the fortified food products of any of the previous embodiments, wherein the product is solid such us rice, pasta, macaroni, or a meat product.

Certain embodiments are related to a method for extending the shelf life of a food material wherein the food material is treated with a food additive according to any of the previous embodiments.

Certain embodiments are related to a method to enhance production of enterolactones in human gut, said method comprising administering orally the dietary supplement of any one of the previous embodiments to a human being on daily basis.

Certain embodiments are related to a method to decrease risk of cancer in a mammal, said method comprising administering orally the dietary supplement of any one of the previous embodiments to a human being on daily basis.

EXAMPLES

Example 1

A concentrated alcohol-wood extract containing following lignan mixture was prepared by extracting chipped knot wood of *Picea abies* with an extraction solution composing of propylene glycol. The lignan extract contained 7.5 wt-% lignan mixture presented in table 1:

TABLE 1

| Lignan mixture: | |
|---|---|
| Lignan | Amount, % W |
| Hydroxymatairesimol | 5-6 |
| Secoisolaricesinol | 0.2-0.4 |
| Conidendrin | 0.2-0.4 |
| Liovil | 0.2-0.4 |
| Lariciresinol | 0.1-0.2 |
| Other lignans | 0.2-1 |

Example 2

A concentrated alcohol-wood extract containing a lignan mixture presented in table 1 was prepared by extracting chipped knot wood of *Picea abies* with an extraction solution composing of ethanol and water. The alcohol-water wood extract contained 75 wt-% of lignan mixture presented in table 1.

Example 3

A food additive was prepared containing 80 wt % of caprylic/capric acid (CAS 85536-07-8) and 20 wt-% of alcohol-water wood extract prepared in example 2. Thus food additive contained 15 wt-% of lignan mixture from its dry weight.

Example 4

In a corresponding way as in example 3 other food additives mentioned above may be prepared. Lecithin can be used as a dispersion agent.

Example 6

An alcoholic composition (liquid) was prepared by mixing 10 weight-% of lignan extract prepared according to example 1 with 90 weight-% of 1,3-propanediol (Zemea, Dupont-Tate-Leyle). This composition was administered daily to patients 5-10 drops/day. Cholesterol, LDL, HDL and triglyceride levels were measured from the blood samples of patients after indicated time period.

TABLE 2

| Female | Age cirka. | Chol. | LDL (<3) | HDL (>1) | Triglyserides (<2) | Amount used |
|---|---|---|---|---|---|---|
|  | 60 | 6.2 | 4.2 | 1.61 | 0.90 | 5 drops/day |
|  |  | 5.9 | 3.8 | 1.77 | 0.64 | 8 months |
| Male | 50 | 5.9 |  |  |  | 5 drops/day |
|  |  | 4.5 |  |  |  | 3 months |
| Male |  | 5.2 |  |  |  | 5 drops/day |
|  |  | 4.1 |  |  |  | 12 months |
| Female | 40 | 6.3 |  |  |  | 5 drops/day |
|  |  | 5.5 | 2.8 | 2.35 | 0.94 |  |

It is evident from the results in table 2 that the cholesterol, LDL, HDL and triglyceride levels decreased markedly after using five drops of the composition daily for a period of 3-12 months.

What is claimed is:

1. An alcohol-wood extract for lowering cholesterol level of blood serum in a mammal, said extract comprising an extraction solution and a lignan mixture at a range of 1-50 wt-%, the lignan mixture comprising:
70-80 wt-% 7-hydroxymatairesinol, 3-8 wt-% conidendrin, 1-4 wt-% lariciresinol, 2-5 wt-% liovil, 3-7 wt-% secoisolarisinol, and 0-3 wt-% other lignans.

2. The extract of claim 1, wherein the extract comprises extraction solution from extraction of knot wood wherein the extraction solution is selected from the group consisting of an alcohol and a water-alcohol mixture.

3. The extract according to claim 1, wherein the extract additionally comprises one or more lignan(s) at a range of 0-10 wt-% selected from the group consisting of pinoresinol, nortrachelogenin, matairesinol, juvabiones, their geometric isomers or stereoisomers, and oligolignans.

4. The extract according to claim 2, wherein the extraction solution comprises a monovalent lower alcohol and/or, a divalent lower alcohol and/or a trivalent lower alcohol.

5. The extract according to claim 1, wherein the extract further comprises triterpens or stilbenes selected from the group consisting of betulin, betulonic acid, betulinic acid, betuloinic acid, resveratrol, their geometric isomers and stereoisomers thereof.

6. The extract according to claim 1, wherein the extract further comprises added vitamin(s) or plant lignan(s).

7. The extract according to claim 1, wherein the extract comprises 7.5 wt-% of the lignan mixture.

* * * * *